United States Patent
Frank et al.

(10) Patent No.: US 6,973,205 B2
(45) Date of Patent: Dec. 6, 2005

(54) SCRATCH-RESISTANT COATING FOR A SEMICONDUCTOR COMPONENT

(75) Inventors: Manfred Frank, Nittendorf (DE); Werner Kröninger, Neutraubling (DE); Renate Köpnick, Regensburg (DE); Richard Hummel, Burglengenfeld (DE); Reinhard Fischbach, München (DE); Heinz Opolka, Regensburg (DE)

(73) Assignee: Infineon Technologies AG, Munich (DE)

( * ) Notice: Subject to any disclaimer, the term of this patent is extended or adjusted under 35 U.S.C. 154(b) by 609 days.

(21) Appl. No.: 10/067,176

(22) Filed: Feb. 4, 2002

(65) Prior Publication Data
US 2002/0114496 A1    Aug. 22, 2002

Related U.S. Application Data

(63) Continuation of application No. PCT/DE00/02568, filed on Aug. 2, 2000.

(30) Foreign Application Priority Data
Aug. 2, 1999    (DE)    ............... 199 36 322

(51) Int. Cl.$^7$ ............................................. G06K 9/00
(52) U.S. Cl. .................................................. 382/124
(58) Field of Search .................. 382/115, 124–127; 340/5.53, 5.83; 257/629, 630, 631, 632

(56) References Cited

U.S. PATENT DOCUMENTS

| | | |
|---|---|---|
| 5,479,049 A | 12/1995 | Aoki et al. |
| 5,963,679 A | 10/1999 | Setlak |
| 6,091,132 A * | 7/2000 | Bryant ........................ 257/632 |

FOREIGN PATENT DOCUMENTS

| | | |
|---|---|---|
| EP | 0 152 744 A1 | 8/1985 |
| EP | 0 457 398 A2 | 11/1991 |
| EP | 0 791 899 A2 | 8/1997 |
| EP | 0 915 373 A1 | 5/1999 |
| JP | 57 027 790 | 2/1982 |
| JP | 59-176330 | 10/1984 |
| JP | 61-129733 | 6/1986 |
| JP | 4-231803 | 8/1992 |
| JP | 06 232 379 A | 9/1994 |
| JP | 9 251 530 | 9/1997 |
| JP | 11-111524 | 4/1999 |
| JP | 11 135 691 A | 5/1999 |
| WO | 98/03934 | 1/1998 |

* cited by examiner

Primary Examiner—Vikkram Bali
(74) Attorney, Agent, or Firm—Laurence A. Greenberg; Werner H. Stemer; Ralph E. Locher

(57) ABSTRACT

To increase the scratch resistance of a surface passivation, in particular, for fingerprint sensors, a antifrictional layer is applied to reduce the shearing forces. The antifrictional layer includes fat, oil, surfactants and/or wax. The antifrictional layer is preferably an emulsion including water, paraffin oil, propylene glycol, stearic acid, palmitic acid, TEA, beeswax, carbormer 954, methylparaben, propylparaben and possibly perfume.

5 Claims, 1 Drawing Sheet

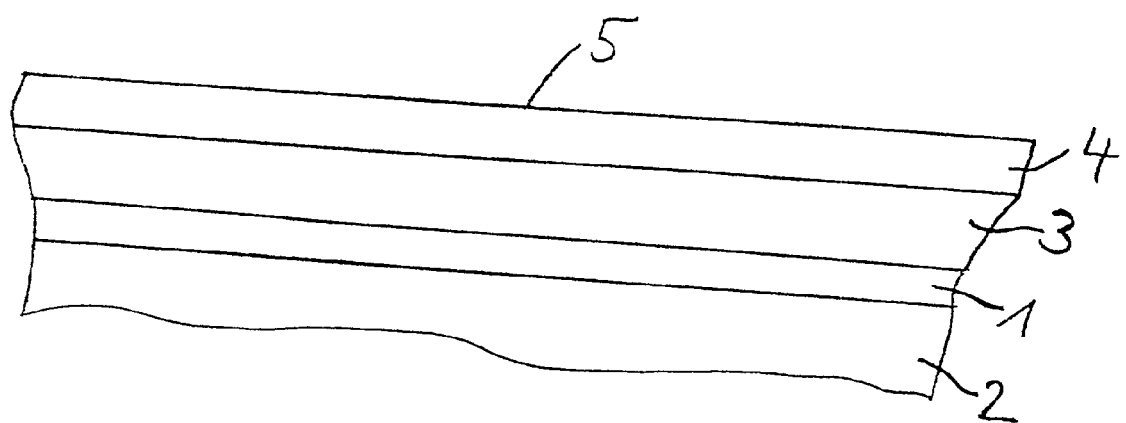

SCRATCH-RESISTANT COATING FOR A SEMICONDUCTOR COMPONENT

CROSS-REFERENCE TO RELATED APPLICATION

This application is a continuation of copending International Application No. PCT/DE00/02568, filed Aug. 2, 2000, which designated the United States.

BACKGROUND OF THE INVENTION

Field of the Invention

The present invention relates to a scratch-resistant coating for a semiconductor component, which in particular can be used as the supporting surface for measuring fingerprints.

Semiconductor components that are exposed to environmental influences, and in particular, to mechanical wear require a particularly hard, scratch-resistant passivation. In fingerprint sensors, the finger pad is rested on a supporting surface. In this manner, the supporting surface is exposed to mechanical wear that significantly impairs the properties of the fingerprint sensor. With fingerprint sensors that operate according to the capacitive measurement method, it is important to keep the distance, between a resting finger pad and the conductor planes in the semiconductor component of the sensor, constant within a narrow tolerance even after the sensor has been used for a relatively long time. Conventional passivation layers made of silicon oxide or silicon nitride, such as those that are usually used in semiconductor technology, cannot be suitably used when the surface of the component is subjected to relatively great loading. Using thicker passivation layers or customary passivation materials such as polyimide, for example, is not suitable, since thicker passivations reduce the sensitivity of the sensor.

Testing that has been performed on fingerprint sensors that have been passivated with customary passivation layers has shown that the finger supporting surface of such sensors is required to have a high scratch resistance.

SUMMARY OF THE INVENTION

It is accordingly an object of the invention to provide a semiconductor component having a surface coating which overcomes the above-mentioned disadvantages of the prior art apparatus of this general type.

In particular, it is an object of the invention to provide a coating for a semiconductor component which, even when the coating has a small layer thickness and even when the coating is subjected to high loading, is sufficiently hard and scratch-resistant to be used in fingerprint sensors.

With the foregoing and other objects in view there is provided, in accordance with the invention, a semiconductor component including a surface coating formed as an antifrictional layer for providing protection against scratches and mechanical abrasion. The antifrictional layer is formed from a combination of materials including fats, oils, surfactants, and waxes. The antifrictional layer has an upper side forming a supporting surface of a fingerprint sensor for sensing a finger pad.

In accordance with an added feature of the invention, the antifrictional layer contains a silicone oil.

In accordance with an additional feature of the invention, the antifrictional layer contains a perfluoropolyether.

With the foregoing and other objects in view there is also provided, in accordance with the invention, a surface coating formed as an antifrictional layer. The antifrictional layer is an emulsion including water, paraffin oil, propylene glycol, stearic acid, palmitic acid, triethylamine, beeswax, carbormer 954, methylparaben and propylparaben. In accordance with added features of the invention, there is provided, a passivation layer having an upper side; the passivation layer is either a polyimide layer, a silicon oxide layer, a silicon nitride layer, or a double layer having a silicon oxide layer and a silicon nitride layer. The antifrictional layer protects the upper side of the passivation layer against scratches and mechanical abrasion. The antifrictional layer has an upper side forming a supporting surface of a fingerprint sensor provided for sensing a finger pad.

The coating is based on the realization that scratches on a passivation layer are caused by shearing forces that act on the surface. The coating according to the invention is an antifrictional layer, which has the property of reducing such shearing forces to such an extent that damage to the surface is prevented, and if used as intended, wear is greatly reduced. Since this antifrictional layer can be applied very thinly, when it is used, the sensitivity of the capacitively measuring sensor is not reduced. This antifrictional layer is preferably applied to a customary passivation layer of an oxide and/or a nitride.

Other features which are considered as characteristic for the invention are set forth in the appended claims.

Although the invention is illustrated and described herein as embodied in a scratch-resistant coating for semiconductor components, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The sole drawing FIGURE is a cross sectional view of the layers of a capacitively measuring sensor on semiconductor material.

DESCRIPTION OF THE PREFERRED EMBODIMENTS

Referring now to the sole FIGURE of the drawing in detail, there is shown a conductor layer 1 that is located on the upper side of a semiconductor component 2. The FIGURE only shows a portion of the semiconductor component 2, which is illustrated without a specific structure. The conductor layer 1, for example, when constructed as part of a fingerprint sensor, may be divided into a multiplicity of conductor areas arranged in a grid form and corresponding to image points. The conductor layer 1 is covered with a passivation layer 3, which may be, for example, polyimide or a single or double layer of silicon oxide and/or silicon nitride. This passivation layer 3 ensures that the conductor layer 1 is electrically insulated, mechanically protected and kept at a constant distance from the outer surface of the component. To protect the upper side of the passivation layer 3 from scratches and mechanical abrasion, according to the invention, the antifrictional layer 4 is applied. The surface of the antifrictional layer 4, for example, in the case of a fingerprint sensor, represents the supporting surface 5 for a finger pad.

Fats, oils, boundary-/surface-active substances (surfactants) and/or waxes preferably come into consideration as the material for the antifrictional layer. If the antifrictional layer will be applied before the component is fitted into a housing, it is generally necessary to resort to more temperature-resistant materials for the antifrictional layer, because of the greater exposure to high temperatures. These may be, inter alia, synthetic oils or fats (for example silicone oil) or synthetic waxes (for example Teflon wax) or thin layers of a material of the polytetrafluoroethylene group (for example TEFLON™). In the substance group of surfactants, perfluoropolyethers exhibit very good mechanical stability and chemical resistance. In a particularly preferred exemplary embodiment of the antifrictional layer according to the invention, it is formed by an emulsion comprising: water, paraffin oil, propylene glycol, stearic acid, palmitic acid, TEA (triethylamine), beeswax, carbormer 954 , methylparaben and propylparaben. Perfume can be added without any concern.

We claim:

1. A semiconductor component, comprising:
    a surface coating formed as an antifrictional layer for providing protection against scratches and mechanical abrasion;
    said antifrictional layer being formed from a combination of materials selected from the group consisting of fats, oils, surfactants, and waxes; and
    said antifrictional layer having an upper side forming a supporting surface of a fingerprint sensor for sensing a finger pad.

2. The semiconductor component according to claim 1, wherein said antifrictional layer contains a silicone oil.

3. The semiconductor component according to claim 2, wherein said antifrictional layer contains a perfluoropolyether.

4. The semiconductor component according to claim 1, wherein said antifrictional layer contains a perfluoropolyether.

5. The semiconductor component according to claim 4, comprising:
    a passivation layer having an upper side;
    said passivation layer being a layer selected from the group consisting of a polyimide layer, a silicon oxide layer, a silicon nitride layer, and a double layer having a silicon oxide layer and a silicon nitride layer;
    said antifrictional layer protecting said upper side of said passivation layer against scratches and mechanical abrasion; and
    said antifrictional layer having an upper side forming a supporting surface of a fingerprint sensor provided for sensing a finger pad.

* * * * *